United States Patent [19]
Greenwald et al.

[11] Patent Number: 6,032,072
[45] Date of Patent: Feb. 29, 2000

[54] METHOD FOR ENHANCING AND SEPARATING BIOPOTENTIAL SIGNALS

[75] Inventors: Scott D. Greenwald, Norfolk; Philip H. Devlin, Brookline; Charles P. Smith, Medway, all of Mass.

[73] Assignee: Aspect Medical Systems, Inc., Natick, Mass.

[21] Appl. No.: 09/016,104

[22] Filed: Jan. 30, 1998

[51] Int. Cl.$^7$ .................... A61B 5/0476; A61B 5/0478; A61B 5/0488; A61B 5/0492

[52] U.S. Cl. .................... 600/544; 600/383; 600/391; 600/393; 600/394; 600/396; 600/397; 600/546

[58] Field of Search .................... 606/544, 546, 606/509, 383, 391, 393, 394, 396, 397

[56] References Cited

U.S. PATENT DOCUMENTS

| | | | |
|---|---|---|---|
| 4,112,930 | 9/1978 | Feldman et al. | 600/509 |
| 4,170,227 | 10/1979 | Feldman et al. | 600/509 |
| 4,171,696 | 10/1979 | John | 128/731 |
| 4,776,345 | 10/1988 | Cohen et al. | 128/731 |
| 5,193,550 | 3/1993 | Duffin | 128/697 |
| 5,817,030 | 10/1998 | Tarjan et al. | 600/544 |

FOREIGN PATENT DOCUMENTS

| | | |
|---|---|---|
| WO 97/04703 | 2/1997 | WIPO . |
| WO 98/16152 | 4/1998 | WIPO . |

OTHER PUBLICATIONS

Jervice, B. W., "The Removal of Ocular Artefacts from the Electroencephalogram: a renvew", Medical & Biological Engineering & Computing, Jan. 1988, pp. 2–12.

*Primary Examiner*—Lee Cohen
*Attorney, Agent, or Firm*—Hale and Dorr LLP

[57] ABSTRACT

Disclosed is an electrode array (i.e., "sensor") and a method for separating near and far-field signals. In one embodiment a horizontal array is used, and in an alternate embodiment a vertical array is used. The electrode array consists of two well-separated pairs of closely spaced electrodes (and a separate ground element). In a typical application of collecting a channel of EEG, "sensing" electrodes are placed in standard locations (e.g., R and Ctr) with a ground electrode placed elsewhere on the head. The voltage measured between the well-separated sensing electrodes is the far-field dominant (i.e., EEG-dominant) channel. Additional electrodes are placed near each of the two sensing electrodes. (The additional electrodes are immediately lateral to the existing electrodes in the horizontal array, and are immediately above the existing electrodes in the vertical array.) The voltages measured between the pairs of closely spaced electrodes are near-field dominant (i.e., EMG/EOG-dominant) channels. The EEG, EMG and EOG signals can be enhanced by uncoupling them by combining information from all channels. The sensor is connected to a monitor via a patient interface cable (PIC). The sensor contains additional circuitry at the connection site that is used by the monitor to identify the presence and type of sensor, and to configure the monitor to invoke the appropriate software that will apply the method of the current invention to collect and uncouple the EEG, EMG and EOG.

22 Claims, 6 Drawing Sheets

| ELECTRODE | LOCATION |
|---|---|
| R | RIGHT OF THE OUTER MALAR BONE. |
| CTR | HIGH ON THE FOREHEAD. |
| CTR' | DIRECTLY BELOW THE CTR ELECTRODE. |
| R' | DIRECTLY ABOVE THE R ELECTRODE. |

CH1 = R - CTR
CH2 = CTR - CTR'
CH3 = R - R'

METHOD FOR ENHANCING AND SEPARATING BIOPOTENTIAL SIGNALS

BACKGROUND OF THE INVENTION

Anesthetics, sedatives and paralytic agents are frequently used by physicians to control the levels of hypnosis, analgesia and muscle relaxation in patients undergoing surgical or medical procedures, recovering from surgery, or receiving medical treatment. Monitoring the effects of these agents on the patient is useful for ensuring efficacious drug administration to achieve the desired effect as well as to detect (or predict) untoward events. For example, the use of EEG monitoring to measure the effects of anesthetics on the brain is useful to help titrate agents to a desired level of anesthesia and to prevent intraoperative awareness (from underdosing) or hemodynamic depression (from overdosing). In addition, the use of intraoperative EEG monitoring (as quantified, for example, by the Bispectral Index™ which is an index produced by monitoring equipment sold by Aspect Medical Systems, Inc. the assignee of the present application) has been shown to improve the utilization of anesthetics and to improve the speed and quality of patient recovery. Improvements in methods that measure and analyze the effects of anesthetics (as reflected in changes in measured biopotentials) will provide opportunities for enhanced patient care and resource utilization.

The acquisition of high fidelity biopotentials such as the electroencephalogram (EEG), the electromyogram (EMG) or the electrooculogram (EOG) is frequently essential for many diagnostic tests or for patient monitoring. The accuracy of automated analysis of biopotentials is strongly coupled with the signal quality of the acquired data. In addition, the development of algorithms which extract information from biopotentials is bounded by the range of signal features that are uncorrupted by noise. By acquiring higher fidelity signals, additional and more subtle features of the signal are available for analysis.

EEG, EMG and EOG provide useful and complementary information regarding the effect of anesthetics (and other factors) on a patient. The spontaneous EEG as measured using surface electrodes reflects the cortical activity of the brain localized near the electrodes. Cortical activity can be modulated by changes in cortical cellular function (caused by changes in metabolic needs, hypoxia, cooling or drugs) or by changes in function of subcortical structures that communicate with the cortex (e.g., the reticular activation system which organizes sleep activity). In general, as the depth of anesthesia increases to induce unconsciousness, the EEG power increases while the EEG bandwidth decreases. Consequently, the EEG provides a direct measure of the effects of anesthetics on the brain. For example, it has been demonstrated that the EEG (as quantified by the Bispectral Index) correlates with level of sedation and memory in volunteers.

Similarly, basal muscle tone is modulated by the brain and by factors local to a muscle. Unconsciousness induces a state of relaxation which is reflected in decreased nervous stimulation of muscle and thus decreased EMG power. (The muscle's response to transdermal electrical stimulation is frequently used to assess the degree of pharmacological paralysis and can be used to determine if low EMG power is a result of unconsciousness or paralysis.) In contrast, patient movement or grimacing during surgery generates bursts of EMG on the scalp (i.e., sudden increases in EMG power) which may be used by a monitor to detect a state of insufficient anesthesia.

Eye motion and eye blinks generate potentials that are measured by periorbital electrodes. Detection of eye blinks is useful to confirm consciousness while detection of rapid eye motion is generally indicative of sleep. Slow eye rolling is frequently associated with drowsiness. Thus, the EEG, EMG and EOG provide useful information regarding the state of the patient during anesthesia.

Although EEG, EMG and EOG are the resultant signals generated from different sources beneath the skin, these biopotentials mingle on the scalp where surface electrodes are used to collect the signals. Moreover, scalp electrodes are susceptible to artifacts generated by electrode motion.

Although most of the spectral power of the EEG is in frequencies lower than the high frequency EMG, the spectra of the two signals overlap. Nevertheless, one common approach to improving the perceived signal quality of the EEG is to low pass filter the acquired signals to diminish the high frequency EMG in the EEG (and to high pass filter the signals to diminish the effects of the EEG in the EMG). This is a modestly effective approach in improving the signal quality; however, the cost of this approach is the loss of information that exists in the overlapping band between spectra of the EEG and the EMG.

U.S. Pat. Nos. 4,112,930 and 4,170,227 issued to Feldman describe an electrode configuration of two pairs of neighboring electrodes (i.e., 2 well-separated sets of 2 closely spaced electrodes (plus a fifth electrode as a common ground)) for the purpose of collecting ECG and artifact signals in order to detect the presence of electrode motion artifact to prevent false arrhythmia alarms. In U.S. Pat. No. 4,112,930, the configuration is used to extract 1 ECG signal (measured between one electrode from each pair) and 2 artifact signals (each measured between electrodes within a pair). Alternatively, in U.S. Pat. No. 4,170,227, the same configuration is used to measure 2 ECG signals (1 being the same as above, and the second being between the remaining 2 electrodes). In this case, an artifact signal is derived from the 2 ECG signals by taking their difference.

In both patents issued to Feldman, the presence of artifact is detected in the artifact signal to inhibit processing of the ECG signal (and to disable arrhythmia alarms). The artifact is NOT used to reduce artifact in the ECG signal, but Feldman suggests that one could use the artifact signal to "restore" the ECG signal. Feldman expressly describes a method and apparatus of collecting the signals to detect baseline wander.

Feldman, in an article entitled "A new electrode system for automated ECG monitoring", (Computers in Cardiology, 1979, pp285–288) reported on the performance of his baseline artifact detection system in rejecting false arrhythmia alarms. Here he also introduces the "Smart bi-lectrode", a concentric pair of electrodes (i.e., a center disc surrounded by an annulus). The use of a concentric pair of electrodes was also described in U.S. Pat. No. 3,868,947 issued to Hoslinger. Hoslinger, however, used the 2 pairs of concentric electrodes for artifact compensation (not artifact detection like Feldman). Hoslinger connects together and grounds the outer annulus of each concentric pair. Hoslinger only describes the configuration of the concentric electrodes, with the outer electrodes being connected together and to ground.

In International Application No. PCT/US95/14889 filed by Albrecht, an apparatus and method is described for using related signals from multiple electrodes to reduce noise in ECGs. This PCT application describes a method of injecting high frequency current in order to extract electrode impedance and respiration information while the ECG and baseline wander is simultaneously collected. To do this, multi-segmented electrodes are used in which 3 outer annular segments closely surround a central disc.

The method taught by Albrecht assumes a deterministic, repeating signal (like an ECG) i.e., the data is processed by aligning epochs (of individual beats) relative to a repeating characteristic of the signal (e.g., the R wave), calculating the correlation among all channels for a given beat, averaging the correlation over the recent set of beats, and using this correlation noise measure to select the combination of input channels that will produce a noise-reduced version as an output. This process is obviously not applicable to processing a random, non-repeating signal (like the EEG).

Other prior art describes methods of adaptively removing one signal from another by estimating a transfer function between primary and secondary signals, predicting the "noise" component in the primary signal using the transfer function applied to the secondary signal, and subtracting the predicted noise from the measured signal.

It is therefore a principal object of the present invention to provide a means to collect and uncouple the EEG, EMG and EOG in order to enhance the fidelity of these desired signals.

Another object of the present invention is to provide an electrode designed to enhance the uncoupling of the EEG, EMG and EOG signals.

Still another object of the present invention is to provide a system and method to reduce artifacts due to electrode motion.

SUMMARY OF THE INVENTION

In contrast to the prior art, the present invention presents a method of acquiring and processing signals using an electrode array that enables the separation of EMG (and/or EOG) from EEG while preserving information at all frequencies. This method utilizes the additional information that the effective sources of EMG (and/or EOG) and EEG occur at distinctly different depths under the electrode. In electrical engineering terms, the problem of separating EMG (and EOG) from EEG is the problem of separating a near-field signal from a far-field signal.

The invention consists of both an electrode array (i.e., "sensor") and the signal processing steps associated with separating near and far-field signals. In one embodiment a horizontal array is used, and in an alternate embodiment a vertical array is used. The electrode array consists of two well-separated pairs of closely spaced electrodes (and a separate ground element). In a typical application of collecting a channel of EEG, "sensing" electrodes are placed in standard locations (e.g., R and Ctr) with a ground electrode placed elsewhere on the head. The voltage measured between the well-separated sensing electrodes is the far-field dominant (i.e., EEG-dominant) channel. Additional electrodes are placed near each of the two sensing electrodes. (The additional electrodes are immediately lateral to the existing electrodes in the horizontal array, and are immediately above the existing electrodes in the vertical array.) The voltages measured between the pairs of closely spaced electrodes are near-field dominant (i.e., EMG/EOG-dominant) channels as explained above. The EEG, EMG and EOG signals can be enhanced by uncoupling them by combining information from all channels. The sensor is connected to a monitor via a patient interface cable (PIC). The sensor contains additional circuitry at the connection site that is used by the monitor to identify the presence and type of sensor, and to configure the monitor to invoke the appropriate software that will apply the method of the current invention to collect and uncouple the EEG, EMG and EOG.

The unique features of the proposed system and method are:

1) the focus of the present invention is in uncoupling different physiological signals in order to enhance the fidelity of each while the prior art focuses on eliminating electrode motion artifact in ECG recordings;

2) the adaptive technique of the present invention does not rely upon a source model (i.e., like traditional source-consistency filtering) or on utilizing a transfer function between the channels (i.e., like traditional adaptive filtering); and 3) use of a vertical electrode array.

BRIEF DESCRIPTION OF THE DRAWINGS

FIG. 3($b$) is a schematic view of an alternate embodiment of the electrode array shown in FIG. 3($a$).

FIG. 3($c$) is a schematic view of an alternate embodiment of the electrode array shown in FIG. 3($a$).

FIG. 3($d$) is a schematic view of a preferred embodiment of the vertical electrode array shown in FIG. 1.

DETAILED DESCRIPTION OF THE PREFERRED EMBODIMENT

The present invention is a novel electrode array and system and method for measuring and uncoupling the body's biopotentials.

Figure 1:
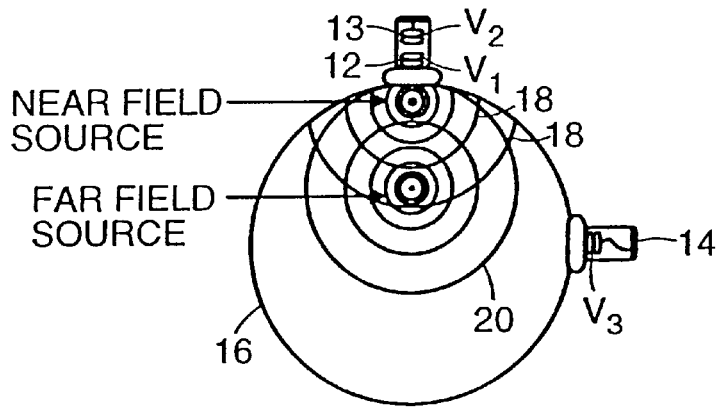
FIG. 1 is a schematic representation of electrode positions for a vertical electrode array of the present invention positioned around a head.
Figure 2:
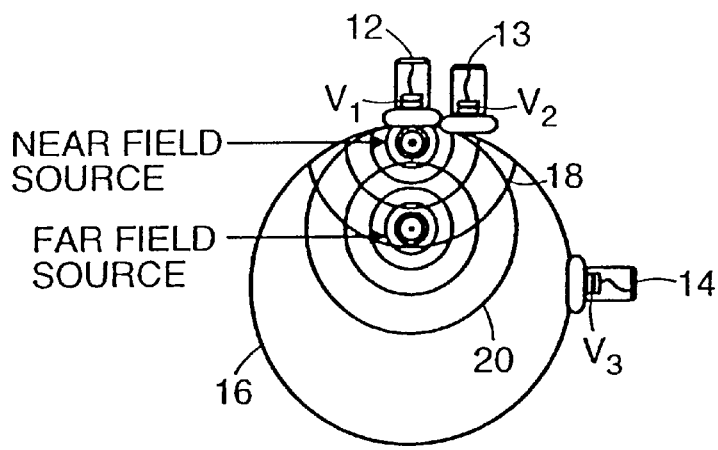
FIG. 2 is a schematic representation of electrode positions for a horizontal electrode array of the present invention positioned around a head.

FIGS. 1 and 2 demonstrate two distinct configurations of electrodes 12, 13, and 14 placed on the surface of a body 16 (i.e., the scalp of a head) which are suitable for collecting biopotentials in a manner that enables the separation of the near-field and far-field signal components. The two sets of concentric circles 18, 20 in each figure represent the set of isopotential lines generated from an effective current dipole at the center of the fields. As indicated, the source located towards the center of the sphere represents a far-field source, while the source located towards the surface of the sphere represents a near-field source (because the sources are far and near the electrode, respectively).

The principle of operation behind separating a near-field signal from a far-field signal is based on the fact that the contributions of the near and far-field electric fields to voltages measured on the body differ at electrode sensing sites placed at different distances from the effective sources of the fields. The voltage measured between a pair of electrodes represents the difference in the measured fields between the two recording sites. The magnitude of the electric field generated from a current dipole falls inversely to the square of the distance from the dipole. Thus, a far-field signal will be similar at positions slightly different from each other. However, the differences in the near-field signals measured at the same set of positions will be much greater (unless the source is equidistant from the two electrode sensing sites). This relative difference in the spatial rate of change of near-field signals vs. far-fields signals enables the separation of near and far-field components within measured signals.

Electrodes 12, 14 will measure both the near and far-field sources, as depicted in FIGS. 1 and 2. If the power of the far-field source is strong relative to the power of the near-field source, then the voltage across a pair of well-spaced (center to center spacing should be between 2.5 inches and 12 inches and preferably approximately 4 inches) electrodes 12, 14 will reflect primarily the far-field source (e.g., the EEG from distant brain cortex). As electrodes of a pair come closer together, the far-field signal becomes increasingly similar at both electrode locations. However, the near-field signal may well be different at the electrode locations. Thus, voltages measured between a pair of closely spaced (center to center spacing should be 2.5 inch or less and preferably 0.4 inches or less) electrodes 12, 13 will reflect primarily the activity of the near-field source (e.g., EMG from nearby muscle). The closely-spaced sensing elements may be displaced horizontally on the recording surface (electrodes 12 and 13 in FIG. 2) or vertically from the recording surface (electrodes 12 and 13 in FIG. 1) or displaced both horizontally and vertically from each other. By simultaneously collecting both EEG-dominant signals (from distant electrodes) and EMG-dominant signals (from close electrodes), higher fidelity EMG and EEG signals can be calculated from a combination of the input signals.

Figure 3A:
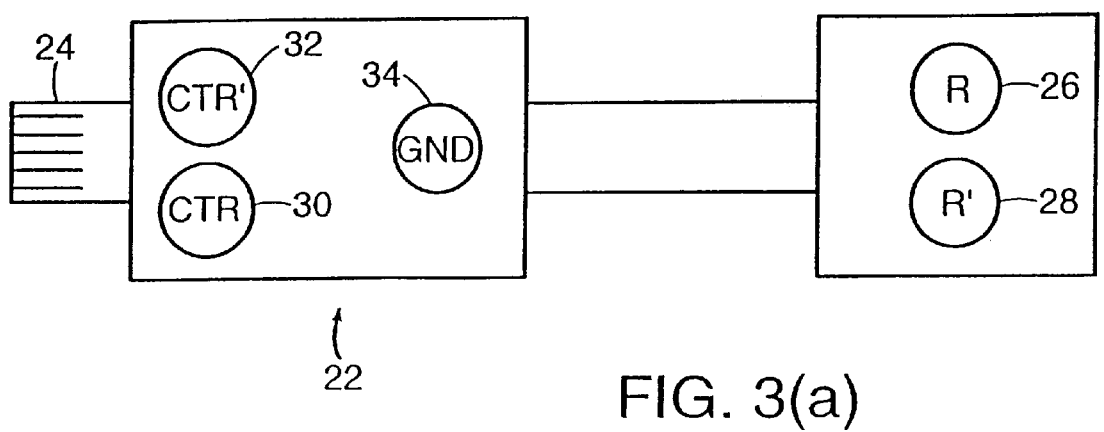
FIG. 3($a$) is a schematic view of a preferred embodiment of the horizontal electrode array shown in FIG. 2.
Figure 4:
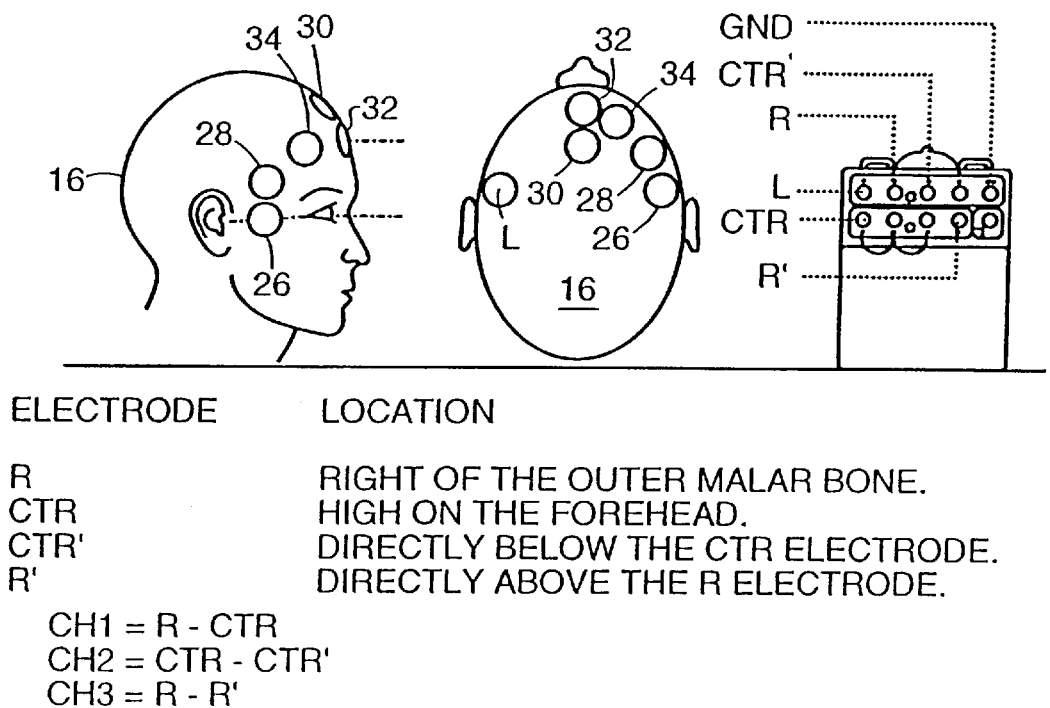
FIG. 4 is a schematic view of a preferred electrode placement of the horizontal electrode array shown in FIG. 3($a$).

FIG. 3(a) presents a schematic view of the horizontal electrode array which could be used to achieve the electrode placement shown in FIG. 2. The array consists of five (5) sensing elements embedded in a single sensor 22. The elements are labeled R, R', Ctr, Ctr' and gnd which refer to Right (R) 26, Right-prime (R') 28, Center (Ctr) 30, Center-prime (Ctr') 32 and Ground 34 locations, respectively as shown in FIG. 4. Each sensing element is connected to printed circuitry that extends to the connector 24. The sensor 22 is connected to a monitor (not shown) via a patient interface cable (PIC) (not shown). There is additional circuitry at the connector 24 that can be used by the monitor to identify the type of sensor attached to the monitor. The additional circuitry is described below.

Figure 3B:
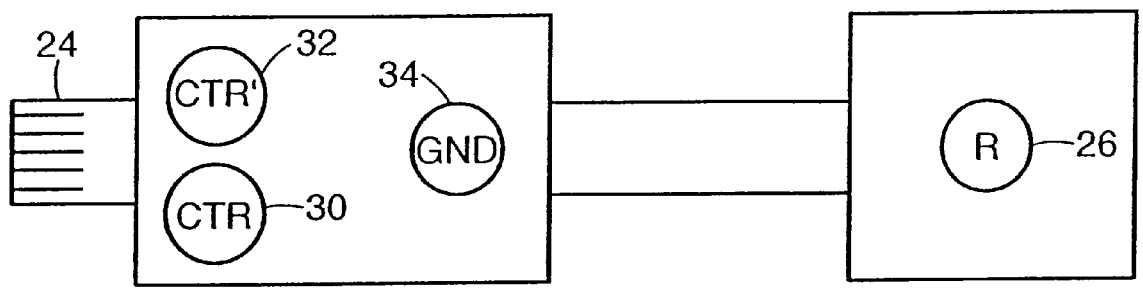
Figure 3C:
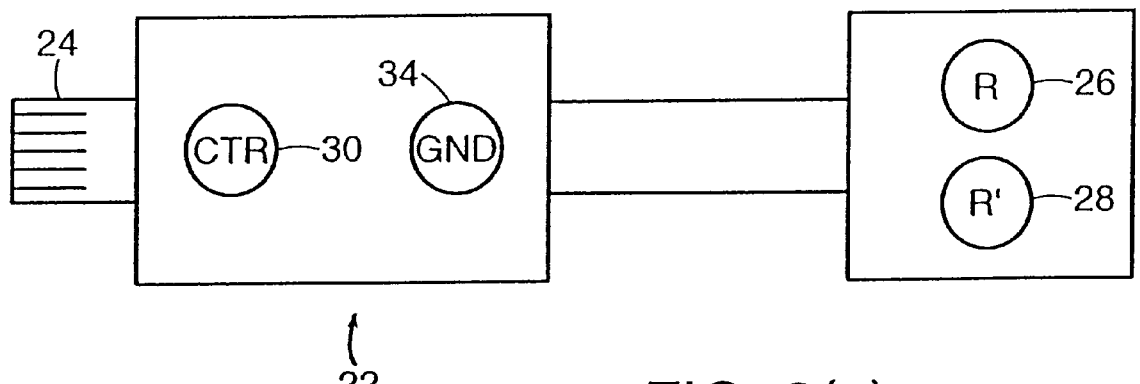
Figure 3D:
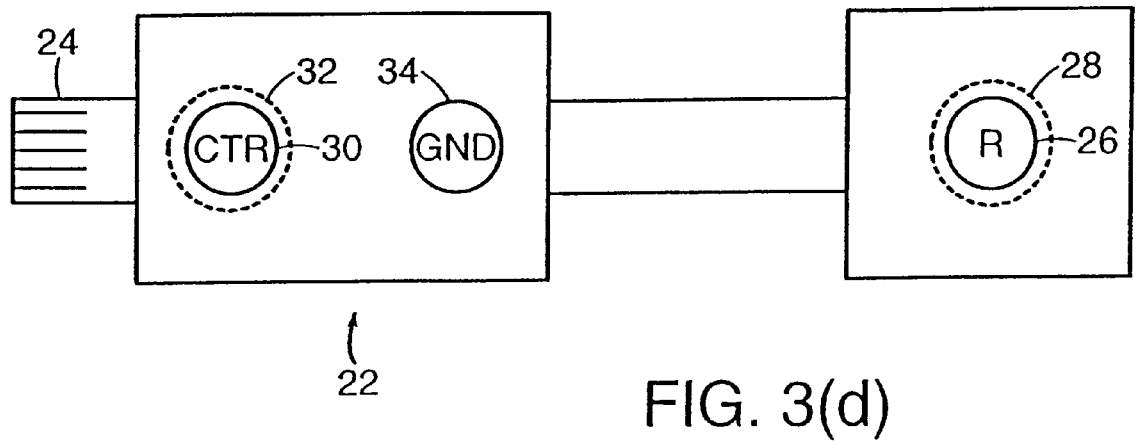

FIG. 3(b) shows an alternate embodiment of the electrode array shown in FIG. 3(a) in which there are two center electrodes and one lateral electrode. In the embodiment shown in 3(c) there are two lateral electrodes and one center electrode. Finally, the embodiment of the sensor shown in FIG. 3(d), includes a center electrode with two electrode elements in vertical alignment and a lateral electrode also with two electrode elements in vertical alignment. An added advantage of this embodiment is that a voltage source (near or far field) cannot be equidistant from both sensing elements.

FIG. 4 is a schematic view of the preferred positioning of the sensor 22 on the scalp of a patient. The sensor 22 is affixed to the patient's forehead so that the center elements 30, 32 rest in the center of the forehead, while the side elements 26, 28 rest near the (right) malar bone. (If desired, the sensor could be inverted to monitor the biopotentials relative to the left side of the head.) The ground element 34 is positioned between the center and side pairs. The voltages measured between the closely spaced pairs of electrodes (i.e., Ctr-Ctr' and R-R') are the near-field dominant signals. The voltage measured between any distantly spaced pair of electrodes (e.g. R-Ctr) is a far-field dominant signal.

Figure 5:
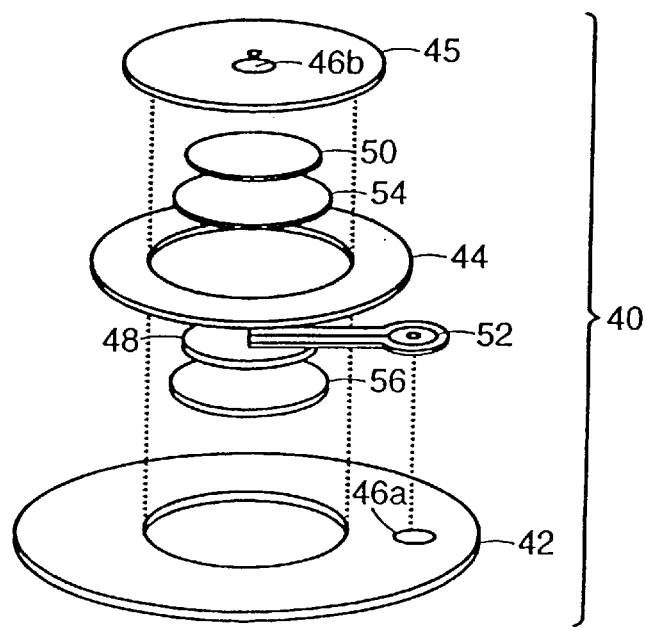
FIG. 5 is a schematic view of a preferred embodiment of a multi-tiered element used within the vertical electrode array shown in FIG. 1.
Figure 6:
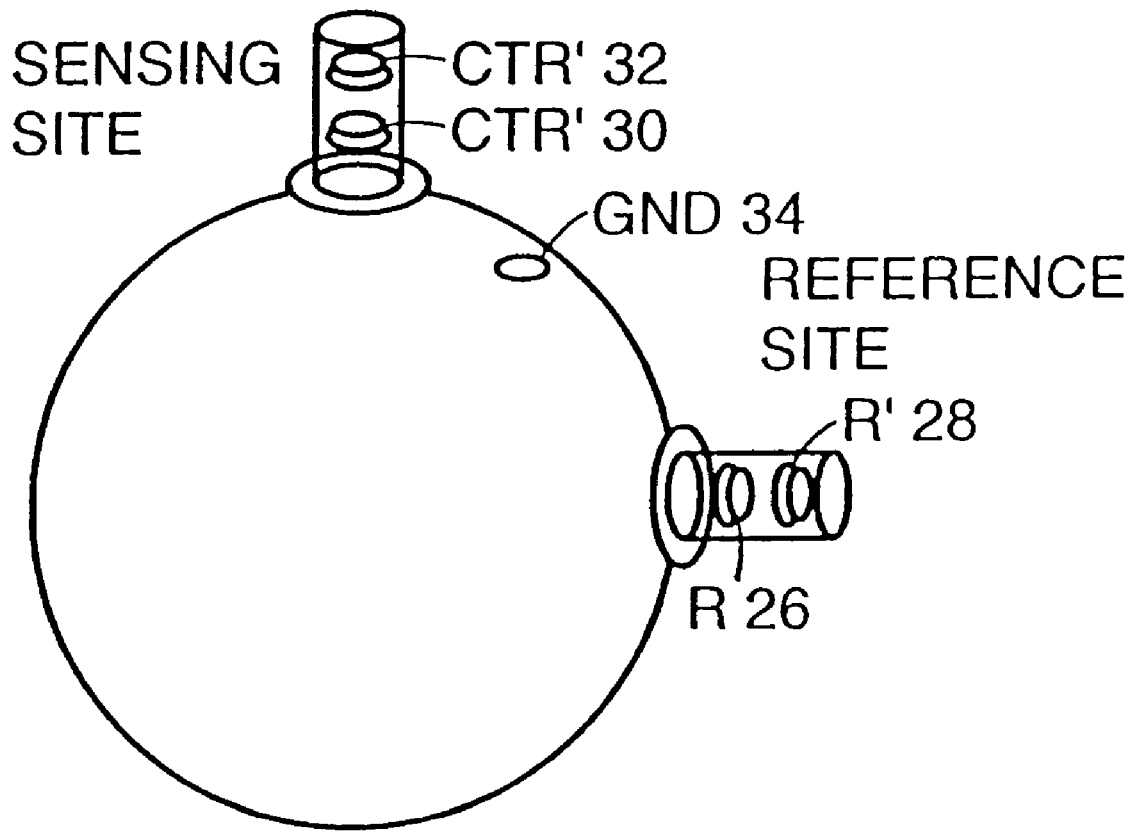
FIG. 6 is a schematic view of a preferred electrode placement of the vertical electrode array shown in FIG. 1.

FIG. 5 shows a preferred embodiment of one multi-tiered element 40 used within a vertical electrode array. As described below the multi-tiered element includes a pair of electrode elements separated by a spacer within a housing. FIG. 6 shows a preferred positioning of multi-tiered elements 40 of a vertical array using 2 multi-tiered elements 40 (and a fifth electrode as a separate ground). One multi-tiered element 40 would be affixed to the center of the patient's forehead (Ctr), while a second element would be affixed to rest near the right malar bone (R). The ground element (gnd) is affixed between the center and side locations. The preferred construction of this array would be embedded within a single piece sensor in a fashion similar to the horizontal sensor 22 so as to enable a similar connection to the monitor to obtain the benefits therefrom. The voltages measured between the closely spaced pairs of electrodes (i.e., Ctr-Ctr' and R-R') are the near-field dominant signals. The voltage measured between a distantly spaced pair of electrodes (R-Ctr) is the far-field dominant signal.

Referring to FIG. 5, the cylindrical housing is constructed in layers. The primary layers making up the walls of the housing are a stack of two rings 42, 44 of single-sided adhesive foam. In a preferred embodiment, the foam is a 1/16" thick, single-sided adhesive-backed, polyethylene foam. The rings have equal inner diameters and are aligned along their centers. The preferred inner diameter of each annulus is 0.6 inches. The two rings have a height sufficient to enable the encasing of electrode elements 48, 50 and spacers 54, 56 within its walls. The adhesive bottom of the larger, bottom annulus 42 is used to attach the electrode array to the patient skin. The top of the bottom annulus 42 provides a footprint for the portion above, and provides a site for the electrical connection for the bottom electrode element 48. In the embodiment shown in FIG. 5, the outer diameter is preferably between 1 and 1.25 inches. In other embodiments, the housing is rectangular with comparable dimensions. The adhesive bottom of the smaller, top annulus 44 fixes to the top of the bottom annulus 42. The top of the top annulus 44 provides a platform for a stiff disc 45 also made of the same foam. This disc 45 acts as the top of the electrode array and provides a site for the electrical connection for the top electrode element 50. The preferred electrical connectors for the bottom and top electrode elements are the commonly used stud "pajama snap" 46a, 46b.

The preferred type of electrode element is the commonly used silver/silver chloride "button" or "pellet." The top electrode element 50 is incorporated in the top of the electrode housing, making electrical contact via a stud snap. The bottom electrode element 48 is attached to a thin film printed circuit conductor 52. The opposite end of this conductor extends between the foam layers of the electrode housing and is sandwiched along with the bottom adhesive annulus between the mating components of a stud snap embedded in the outer ring.

The cylindrical housing is filled with a conductive substance. The preferred conductive substance 10% salt content liquid hydrogel.

One spacer 54 separates the pair of electrode elements 48, 50 while a second spacer 56 separates the bottom electrode element from the skin. Both spacers 54, 56 are preferably porous, compliant, non-conductive spacers that permit free flow of the liquid gel to fill the spacing gap. This design provides an electrical resistivity between electrodes which is similar to the resistivity between the skin interface and the bottom electrode 48. The spacers can be manufactured, for example, by simply stamping discs out of Velcro material. The backing of the Velcro material is porous; moreover, the Velcro material provides the necessary spacing and secures the gel within the space. The preferred Velcro thickness (i.e., spacing) is approximately 0.07 inches.

The multi-tiered electrode element 40 is placed on a strip of pre-formed plastic with the adhesive of the bottom annulus 42 affixed to the strip. The preferred plastic is one which readily releases the electrode element when the bottom annulus is gently peeled away. This design extends the life of the electrode element by retarding the drying of the conductive substance.

Figure 7:
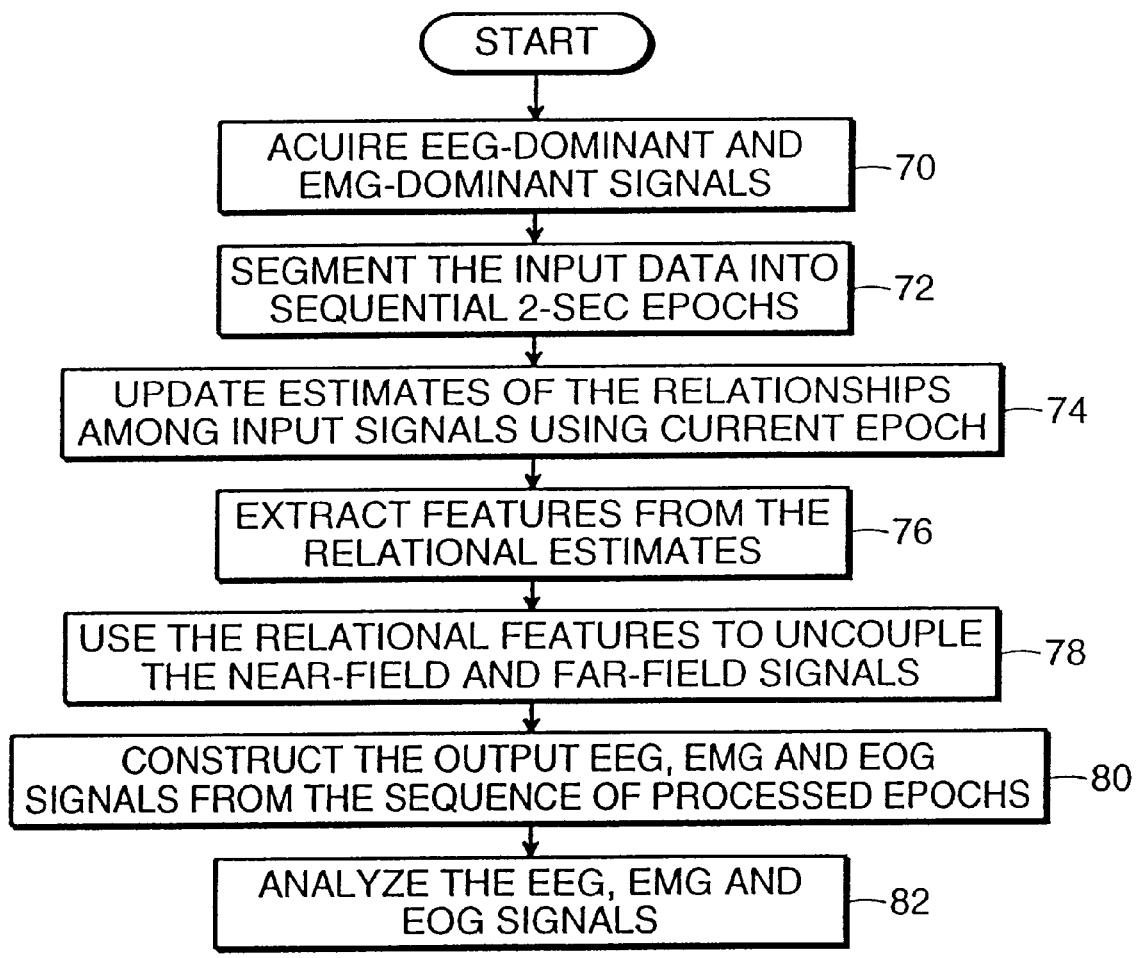
FIG. 7 is a flow chart of the steps performed by the method of the present invention to extract signals.

Referring to FIG. 7 the steps performed to process the signals to extract the near (EMG/EOG) and far (EEG) field signals from the acquired signals will now be described. In step 70, the system simultaneously collects one or more EEG-dominant (i.e., primary) signals and one or more EMG-dominant (i.e., secondary) signals. The CPU in the monitor of the system or the CPU in a computer attached to the system then processes the signals in step 72 using sequential epochs i.e., finite data segments (e.g., 256 samples per channel sampled at 128 samples per second). Next in step 74, the CPU creates and updates estimates of the relationships among the signals with each new epoch (i.e., update estimates of the power spectra of each signal and the cross-spectra between each EMG-dominant channel with each EEG-dominant channel). Then, in step 76 the system derives information (i.e. the coherence) from the relational estimates (i.e., the coherence between the primary and secondary signals).

The system applies the derived information in step 78 to separate the far-field EEG from the near-field EMG (and near-field eye (EOG)) within the current epoch as will be described below with respect to FIG. 8. To do this, the system creates an enhanced EEG signal by reducing the power in the primary signal at each frequency by scaling each frequency component by the maximum coherence between the primary signal with each of the secondary signals. The system then creates a difference signal by subtracting the enhanced EEG signal from the original EEG-dominant signal. The difference signal contains both low-frequency EOG artifact and high frequency EMC. An enhanced EMG signal is then created by high pass-filtering the difference signal (e.g., using a 3-pole Butterworth High Pass Filter with the 3 dB corner frequency at 20 Hz). An enhanced EOG signal is created by low pass filtering the difference signal (e.g., using a 3-pole Butterworth Low Pass Filter with the 3 dB corner frequency at 20 Hz).

In step 80 the system constructs the noise-reduced output EEG, EMG and EOG signal from the sequence of processed epochs by performing inverse Fast Fourier Transforms. Finally in step 82, the system processes the enhanced EEG, EMG and EOG signals to, among other purposes, detect eye blinks and significant EMG power as adjuncts to measuring a patient's state of consciousness.

Figure 8:
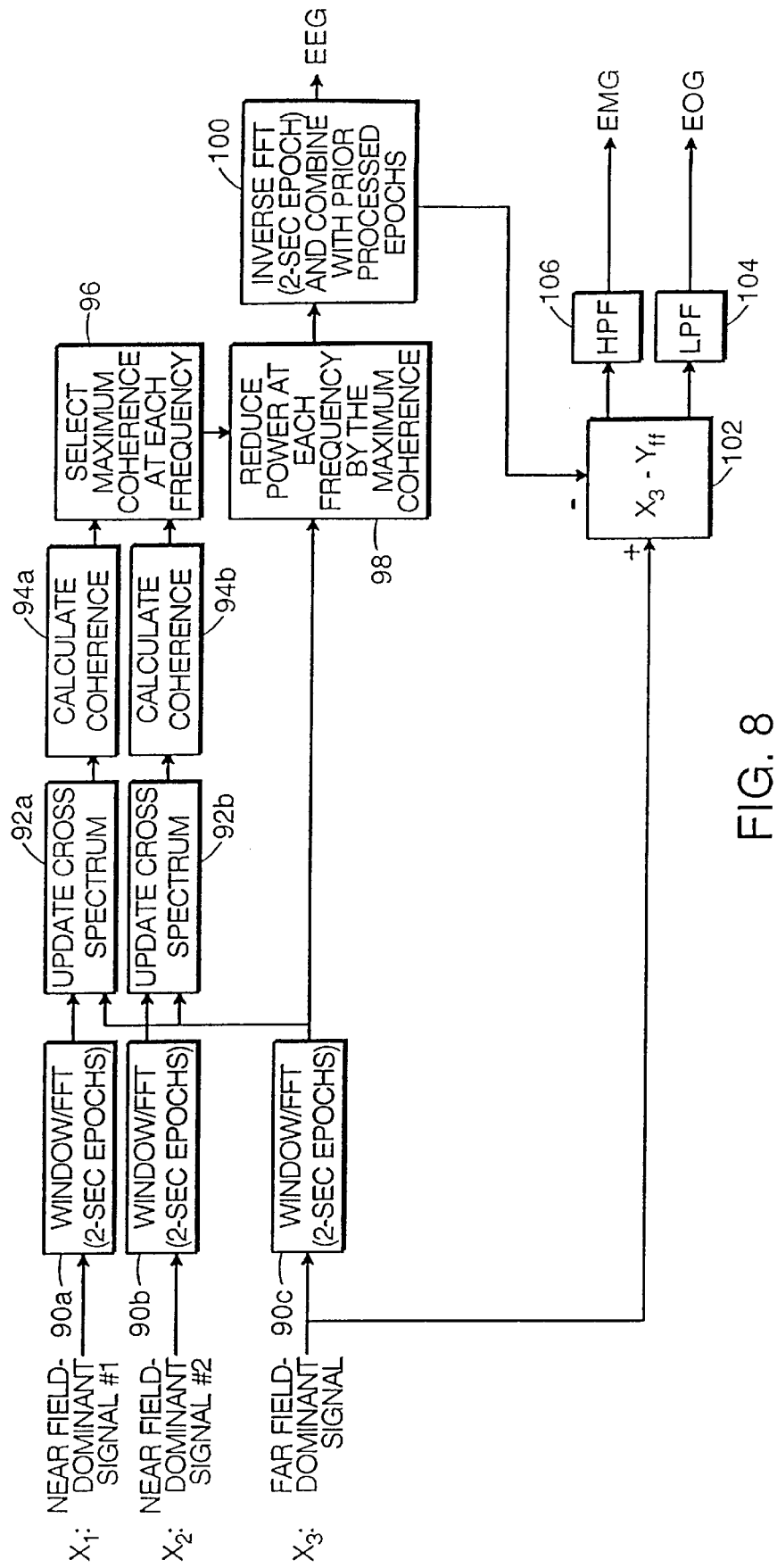
FIG. 8 is a flow diagram of the flow of signals through the system and method of the present invention.

Referring to FIG. 8, the signal processing of the signals derived in the present invention will now be described. The near-field dominant signal #1 and near-field dominant signal #2 are the voltages measured between closely spaced center electrodes (i.e., Ctr-Ctr') and closely spaced lateral electrodes (i.e., R-R'), respectively. The far-field dominant signal is the voltage measured between one center and one lateral electrode (i.e., R-Ctr). (The near-field dominant signal contains primarily EMG and EOG. The far-field dominant signal contains primarily EEG. In the event that only EMG and EEG information is needed then the array could include either two center and one lateral electrode as shown in FIG. 3(*b*), or two lateral and one center electrode as shown in FIG. 3(*c*).) These signals are processed simultaneously by using K sequential, 75% overlapping, 2-second epochs (where K, the number of epochs used in the spectral estimates, is typically 8) in steps 90*a*, 90*b*, 90*c*. The use of overlapping epochs decreases the variance of the subsequent spectral estimation.

With each new 0.5 second of data, the system creates a new epoch for each signal using the most recent 2-seconds of data. For each signal, the mean of the $k^{th}$ 2-second epoch of data is calculated using:

$$\bar{x}_s^k = \frac{1}{N}\sum_{i=0}^{N-1} x_s^k[i]$$

and subtracted from the original epoch:

$$x'^k_s[i] = x_s^k[i] - \bar{x}_s^k \text{ for } i=0,1,2,\ldots,N-1$$

where $x_s^k[i]$ is the $i^{th}$ of N samples within the $k^{th}$ epoch from signal s (where s=1,2 or 3). The preferred number of samples is 256 (i.e., 2 seconds of data sampled at 128 samples per second). The resultant zero-mean epoch is multiplied by a Hanning window to reduce the effects of discontinuities at the edges of the epochs:

$$x''^k_s[i] = w[i] \cdot x'^k_s[i] \text{ for } i=0,1,2,\ldots,N-1$$

where $$w[i] = \frac{1}{2}\left[1 - \cos\left(\frac{2\pi i}{N-1}\right)\right], \quad \text{for } i = 0, 1, 2, \ldots, N-1$$

The resultant windowed epoch is then transformed from the time-domain into the frequency-domain using the Fourier Transform:

$$X''^k_s[m] = \sum_{i=0}^{N-1} x''^k_s[i] \cdot e^{-j\frac{2\pi i m}{N}}, \quad \text{for } m = 0, 1, 2, \ldots, N-$$

where $j=\sqrt{-1}$. The frequency resolution is $f_s/N$, where $f_s$ is the sampling rate (in samples per second). This results in a frequency resolution of 0.5 Hz in the preferred embodiment. The preferred implementation of the Fourier Transform uses the Fast Fourier Transformation (FFT) technique described in *Theory and Application of Digital Signal Processing*, L. R. Rabiner and B. Gold, Prentice-Hall, Englewood Cliffs, N.J. 1975 p.357–381.

The power spectrum of each signal is estimated using the most recent K epochs:

$$S_{ii}[m] = \frac{1}{K \cdot N} \sum_{k=0}^{K-1} (X_i''^k[m])^* \cdot X_i''^k[m],$$

$$\text{for } i = 1, 2, 3; \; m = 0, 1, 2, \ldots, N-1$$

where (*) denotes the complex conjugate.

Likewise, the cross-spectrum between each near-field dominant signal (i.e., signals 1 and 2) with the far-field dominant signal (i.e., signal 3) is updated in steps 92a, 92b using the most recent K epochs:

$$S_{i3}[m] = \frac{1}{K \cdot N} \sum_{k=0}^{K-1} (X_i''^k[m])^* \cdot X_3''^k[m], \text{ for } i = 1, 2; \; m = 0, 1, 2, \ldots, N-1$$

The coherence of two signals is an estimate (from 0 to 1) that describes the consistency of the power and phase relationships between the signals over multiple epochs. The coherence is derived in steps 94a, 94b from the estimates of the power and cross-spectra:

$$C_{i3}[m] = \frac{|S_{i3}[m]|}{\sqrt{S_{ii}[m] \cdot S_{33}[m]}}, \text{ for } i = 1, 2; \; m = 0, 1, 2, \ldots, N-1$$

A weighting function used to scale the power of the far-field dominant epoch is derived from the coherence functions. The coherent portion of the relationship between a near-field dominant signal and far-field dominant signal is assumed to be due to near-field activity. Thus, the weighting function of the preferred embodiment is derived by selecting the maximal coherence between each near-field dominant signal with the far-field dominant signal at each frequency and subtracting that value (representing the near-field activity) from 1 (i.e., perfect coherence). That is, $$W[m] = 1 - Max(C_{13}, C_{23}), \text{ for } m = 0, 1, 2, \ldots, N-1$$

Alternate and similar weighting functions should be obvious to those skilled in the art. The power at each frequency in the original far-field dominant epoch is scaled by the weighting function defined above:

$$\hat{X}_3^k[m] = W[m] \cdot X_3^k[m], \text{ for } m = 0, 1, 2, \ldots, N-1$$

where $X_3^k[m]$ is the $m^{th}$ frequency component of the Fourier Transform of the unmodified version of the $k^{th}$ epoch. The resultant scaled Fourier Transformation of the epoch is then converted back from the frequency domain into the time domain using the Inverse Fourier Transform in step 100 (as implemented using the Fast Fourier Transformation technique):

$$\hat{x}_3^k[i] = \frac{1}{N} \sum_{m=0}^{N-1} \hat{X}_3^k[m] \cdot e^{+j2\pi \frac{im}{N}}, \text{ for } i = 0, 1, 2, \ldots, N-1$$

The central 0.5 seconds of the processed data is the output of the one cycle of processing $$\left(\text{i.e., output } \hat{x}_3^k[i] \quad \frac{N}{2} - \frac{N}{8} \leq i < \frac{N}{2} + \frac{N}{8}\right)$$

Thus, every new 0.5 second of input data creates a new 0.5 second of output data.

The output of this process is the enhanced far-field signal, $y_{ff}[i]$, or the EEG component in this application. The enhanced estimate of the near-field signal, $y_{nf}[i]$, is derived by subtracting the enhanced estimate of the far-field signal from the original far-field dominant signal in step 102. That is, $$y_{nf}[i] = x_3[i] - y_{ff}[i]$$

The desired EOG and EMG components are separated from the enhanced near-field signal by using the approximation that the EOG is principally a low frequency signal, while the EMG is principally a high frequency signal. Thus the EOG component is the output of low pass filtering the enhanced near-field signal in step 104. The preferred embodiment uses a 3rd order Butterworth low pass filter with a 3 dB corner frequency at 20 Hz. Likewise, the EMG component is the output of high pass filtering the enhanced near-field signal in step 106. The preferred embodiment uses a 3rd order Butterworth high pass filter with a 3 dB corner frequency at 20 Hz.

The sensor contains circuitry that may be used by the monitor to configure the instrument to appropriately process the input signals. The preferred embodiment uses a three bit code identification scheme such as the identification scheme described in U.S. patent application Ser. No. 08/545,981 which is assigned to the assignee of the present invention and the teachings of which are incorporated herein by reference. Use of such circuitry enables one machine to identify different electrode configurations and allows different measurements to be taken by the same machine.

While the foregoing invention has been described with reference to its preferred embodiments, various alterations and modifications will occur to those skilled in the art All such alterations and modifications are intended to fall within the scope of the appended clause.

What is claimed is:

1. A method of uncoupling and enhancing near-field and far-field biopotential signals using an electrode array including one pair of closely positioned electrode elements, at least one other electrode element widely spaced from said pair of closely positioned elements and a ground element, said method comprising the steps of:

collecting two or more input signals from said electrode elements;

deriving one or more near-field dominant signals from said input signals collected through two electrodes of said pair of closely positioned electrode elements and deriving at least one far-field dominant signal from said input signals collected through two of said widely-spaced electrode elements;

creating estimates of relationships among the near-field and far-field dominant signals.

2. The method of claim 1 wherein the step of deriving near-field dominant signals comprises deriving near-field dominant signals as measured voltages across said pair of said closely positioned electrode elements.

3. The method of claim 1 wherein the step of deriving one far-field dominant signal comprises deriving a far-field dominant signal as the measured voltage across two widely-spaced electrode elements.

4. The method of claim 1 further comprising the step of segmenting said near-field dominant signals and said far-field dominant signals into a sequence of finite epochs.

5. The method of claim 4 wherein the step of segmenting said near-field dominant signal and said far-field dominant signals comprises segmenting said signals into overlapping, 2-second epochs.

6. The method of claim 1 wherein the step of creating estimates of relationships among the near-field and far-field dominant signals comprises the step of estimating the power spectra of each near-field and far-field dominant signal and of the cross spectra between each pair of near-field and far-field dominant signals.

7. The method of claim 1 wherein the step of creating estimates of relationships among the near-field and far-field dominant signals comprises determining the coherence between each far-field dominant signal with a near-field dominant signal.

8. The method of claim 4 further comprising a step of uncoupling near-field and far-field components from the signals within an epoch, said step of uncoupling comprising the steps of:

attenuating the power at each frequency of the far-field dominant signal in the epoch by weighting each frequency component of a Fourier Transformation of said epoch by a first function of coherences between said far-field dominant signal with each of said near-field dominant signals;

attenuating the power at each frequency of a near-field dominant signal in the epoch by weighting each frequency component of the Fourier Transformation of the epoch by a second function of the coherences between each of said near-field dominant signal with said far-field dominant signal.

9. The method of claim 8 further comprising the step of constructing output near-field signals from said uncoupled near-field components and far-field signals from said far-field components.

10. The method of claim 9 wherein said step of constructing the output near-field and far-field signals from the epochs comprises the steps of:

creating an output far-field signal from the far-field dominant signal by transforming a weighted spectra of the epoch back into the time domain using an inverse Fourier Transformation of said epoch to create a first transformed epoch and outputing samples within the transformed epoch that correspond to a time since the last output sample and a beginning of a next overlapping epoch;

creating an output near-field signal from the far-field dominant signal by transforming a weighted spectra of the epoch back into the time domain using an inverse Fourier Transformation of said epoch to create a second transformed epoch and subtracting said time domain signal in said second transformed epoch from said far-field dominant signal;

outputing samples within said second transformed epoch that correspond to a time since an immediately prior output sample and a beginning of a next overlapping epoch.

11. The method of claim 1 wherein said near-field dominant signals are EOG-dominant signals.

12. The method of claim 1 wherein said near-field dominant signals are EMG-dominant signals.

13. The method of claim 1 further comprising the step of using said estimates of relationships to uncouple near-field components from far-field components of said input signals.

14. A method of uncoupling and enhancing near-field and far-field biopotential signals using an electrode array comprising one pair of closely positioned electrode elements and at least one other electrode element widely spaced from said pair of closely positioned electrode elements and a ground element, said method comprising the steps of:

deriving a first far-field dominant signal from one of said pair of closely positioned electrode elements and said widely spaced electrode element;

deriving a second far-field dominant signal from a second electrode element of said pair of closely positioned electrode elements and said widely-spaced electrode element;

deriving one near-field dominant signal by subtracting said first far-field dominant signal from said second far-field dominant signal.

15. A method of uncoupling and enhancing near-field and far-field biopotential signals using an electrode array comprising one pair of closely positioned electrode elements, at least one other electrode element widely spaced from said pair of closely positioned electrode elements and a ground element, said method comprising the steps of:

deriving one or more near-field dominant signals through two electrodes of said pair closely positioned electrode elements and at least one far-field dominant signal through two of said widely spaced electrode elements;

determining relationships between said near-field dominant signals and said far-field dominant signals; and uncoupling near-field components from far-field components in said biopotential signals.

16. An electrode array for acquiring electrical biopotential signals from a recording surface on a living body comprising:

two or more electrode elements positioned in a third dimension from the recording surface;

a spacer positioned between each two adjacent electrode elements for separating each electrode element from the other electrode elements.

17. The electrode array of claim 16 wherein said two or more electrodes and said spacers are encased in a housing.

18. The electrode array of claim 17 wherein said housing is filled with a conductive substance.

19. The electrode array of claim 18 wherein the conductive substance is a solid hydrogel.

20. The electrode array of claim 18 wherein the conductive substance is a liquid gel.

21. The electrode array of claim 16 wherein said electrode elements are connected to a data acquisition device via lead wires through an electrically isolated snap.

22. An electrode array for acquiring electrical biopotential signals from a recording surface on a living body comprising:

a first electrode element and a second electrode element positioned on a single substrate, the center of said first electrode element being separated from the center of said second electrode element by no more than 2.5 inches;

a third electrode element positioned on said single substrate, the center of said third electrode element being separated from the center of said first electrode element by between 2.5 inches and 12 inches.

* * * * *